United States Patent [19]
Schmidt et al.

[11] Patent Number: 5,910,532
[45] Date of Patent: Jun. 8, 1999

[54] MULTISOLVENT-BASED FILM-FORMING COMPOSITIONS

[75] Inventors: Donald L. Schmidt; Robert D. Mussell, both of Midland, Mich.

[73] Assignee: The Dow Chemical Company, Midland, Mich.

[21] Appl. No.: 08/865,536

[22] Filed: May 29, 1997

[51] Int. Cl.$^6$ ..................................................... C08J 3/00
[52] U.S. Cl. ........................ 524/556; 524/816; 524/832
[58] Field of Search .................................... 524/543, 556, 524/816, 832

[56] References Cited

U.S. PATENT DOCUMENTS

| | | | |
|---|---|---|---|
| 3,947,396 | 3/1976 | Kangas et al. | 260/29.3 |
| 3,948,979 | 4/1976 | Patterson | 260/486 R |
| 4,140,664 | 2/1979 | Mizuguchi et al. | 260/29.4 UA |
| 4,544,697 | 10/1985 | Pickelman et al. | 524/458 |
| 4,544,723 | 10/1985 | Upson et al. | 524/347 |
| 4,582,663 | 4/1986 | Pickelman et al. | 264/517 |
| 4,622,360 | 11/1986 | Gomi et al. | 524/507 |
| 4,704,324 | 11/1987 | Davis et al. | 428/308.4 |
| 4,783,224 | 11/1988 | Sako et al. | 148/6.27 |
| 4,784,789 | 11/1988 | Jeschke et al. | 252/174.23 |
| 4,814,101 | 3/1989 | Schieferstein et al. | 252/174.23 |
| 4,839,166 | 6/1989 | Grollier et al. | 424/71 |
| 4,859,384 | 8/1989 | Fibiger et al. | 264/45.1 |
| 4,929,666 | 5/1990 | Schmidt et al. | 524/516 |
| 5,013,769 | 5/1991 | Murray et al. | 523/111 |
| 5,075,399 | 12/1991 | Ahmed et al. | 526/287 |
| 5,098,699 | 3/1992 | Hayama et al. | 424/71 |
| 5,116,921 | 5/1992 | Hsieh | 526/287 |
| 5,130,389 | 7/1992 | Ahmed et al. | 526/240 |
| 5,216,098 | 6/1993 | Ahmed et al. | 526/288 |
| 5,252,692 | 10/1993 | Lovy et al. | 526/342 |
| 5,310,581 | 5/1994 | Schmidt et al. | 427/558 |
| 5,354,481 | 10/1994 | Neff et al. | 210/734 |
| 5,354,806 | 10/1994 | Hsieh | 524/547 |
| 5,464,538 | 11/1995 | Schmidt et al. | 210/490 |
| 5,470,908 | 11/1995 | Schmidt et al. | 524/520 |
| 5,527,853 | 6/1996 | Landy et al. | 524/521 |
| 5,578,598 | 11/1996 | Abe et al. | 514/255 |
| 5,580,650 | 12/1996 | Forgach et al. | 428/304.4 |
| 5,609,862 | 3/1997 | Chen et al. | 424/70.11 |
| 5,639,814 | 6/1997 | Van Buskirk et al. | 524/389 |
| 5,674,934 | 10/1997 | Schmidt et al. | 524/555 |

FOREIGN PATENT DOCUMENTS

| | | |
|---|---|---|
| 0 000 426 | 6/1978 | European Pat. Off. . |
| 44 01 708 A1 | 7/1995 | Germany . |
| 61-012609 | 1/1986 | Japan . |
| 2-215871 | 8/1990 | Japan . |
| 7809940 | 5/1979 | Netherlands . |
| 97/31042 | 8/1997 | WIPO . |

OTHER PUBLICATIONS

Chemical Reg. No. 45076–54–8, 1996.
Chemical Reg. No. 51441–64–6, 1996.
Chemical Reg. No. 63810–34–4, 1996.
Chemical Reg. No. 73082–48–1, 1996.
Chemical Reg. No. 82667–45–6, 1996.
Chemical Reg. No. 93926–67–1, 1996.
Chemical Reg. No. 122988–32–3, 1996.
Chemical Reg. No. 145425–78–1, 1996.
Chemical Reg. No. 149186–03–8, 1996.
Chemical Reg. No. 151938–12–4, 1996.
Chemical Reg. No. 166740–88–1, 1996.
Van Dyk, John W., et al., Ind. Eng. Chem. Prod. Res. Dev., vol. 24, pp. 473–477 (1985).
Daniels, E. S., et al., Progress In Organic Coatings, vol. 19, pp. 359–378 (1991).
Hansen, Charles M., J. Paint Technology, vol. 39, No. 511, pp. 505–510 (Aug. 1967).
Kötz, J., et al., ACTA Polymer, vol. 43, pp. 193–198 (1992).
Ooka, M., et al., Progress In Organic Coatings, vol. 23, pp. 325–338 (1994).
Padget, J. C., Journal Of Coatings Technology, vol. 66, No. 839, pp. 89–105 (Dec. 1994).
Shalbayeva, G. B., et al., Polymer Science U.S.S.R., vol. 26, No. 6, pp. 1421–1427 (1984).

*Primary Examiner*—Erma Cameron

[57] ABSTRACT

Substantially permanent or removable coatings can be prepared from a composition comprising a polymer dissolved or dispersed in a multicomponent medium that contains water, a low-boiling polar organic solvent, and a high-boiling point solvent. The polymer is characterized by containing structural units formed from the polymerization of a polymerizable strong cationic monomer, a polymerizable acid monomer, and optionally a non-interfering monomer. The composition forms a dust-free and tack-free film that can be removed by a combination of water and an organic solvent. The film can also be made resistant to organic solvents as well as acids and bases with the addition of a crosslinking agent to the composition.

20 Claims, No Drawings

MULTISOLVENT-BASED FILM-FORMING COMPOSITIONS

BACKGROUND OF THE INVENTION

The present invention relates to a water-dispersible polymeric composition that can be used to prepare a dust-free and tack-free coating.

Coatings provide protective barriers for a variety of things including floors, automobiles, exteriors and interiors of houses, and human skin. Protective coatings for floors, for example, have been known since the mid 1950s. Many of the early coating materials were applied using petroleum- or naphthene-based solvents and as such were undesirable due to the toxicity and flammability of these solvents.

Water-based synthetic emulsion compositions, such as styrene resin emulsions, styrene-acrylate copolymer resin emulsions, and acrylate emulsions, developed in the early 1960s, gradually replaced organic solvent-based compositions. Although these water-based compositions are less toxic and more environmentally friendly than organic solvent-based compositions, the water-based compositions tend to be slow to set and difficult to remove in an application where removability is desired. Removal of coatings may be desirable because even the most durable coatings tend to deteriorate due to soiling or wear and tear. In other applications, such as protective care products for the skin, the advantages of water-based removable coatings are obvious.

Removable, water-based coatings are known. For example, polymers that contain ammonium carboxylate functionality are water compatible, but become incompatible through the loss of solvent and ammonia.

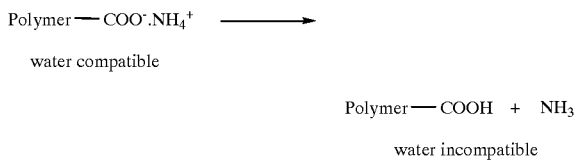

Coatings made by the above-illustrated process can be subsequently removed by contact with an aqueous alkaline liquid, which converts the acid back into the compatible salt.

For example, in U.S. Pat. No. 4,622,360, Gomi et al. discloses a removable water-borne polyurethane resin containing carboxyl groups. Coating compositions can be prepared by adding a polyvalent complex-forming metal to the water-borne resin. The polyvalent metal forms a stable water-dispersible complex with the resin in the aqueous solution. When the dispersion is applied to a floor surface, noxious volatile materials evaporate to allow the polyvalent metal ions to initiate a crosslinking of two or more carboxyl groups, thereby forming a hardened, water-incompatible coating. This hardened coating can be removed, but only with a harsh alkaline solution containing ligands such as ethylene diamine tetraacetic acid.

The ammonium carboxylate coating suffers from several disadvantages: 1) the formulations are malodorous and irritating to the eyes and skin; 2) long set times are required to attain acceptable physical properties of the coating; and 3) the removal or stripping process requires the use of hazardous alkaline liquids.

In view of the deficiencies of the known art, it would be desirable to have a composition that provides a dust-free and tack-free coating that can be removed without the use of harsh solvents in applications where such removal is desirable. It would further be desirable to render such a coating resistant to common organic solvents readily in applications where general solvent resistance is desired.

It would further be useful to have a hypoallergenic, non-toxic, water-based composition that provides a coating that gives long-lasting protection to the skin against sun, dryness, and harsh chemicals.

SUMMARY OF THE INVENTION

The present invention is a composition comprising: a) a polymer that contains strong cationic groups and acid groups; and b) a multisolvent medium that contains water, a low-boiling polar organic solvent which has at least one hydroxy group, is soluble in water in all proportions, and has a boiling point in the range of from about 70° C. to about 134° C.; and optionally a high-boiling solvent, which has a boiling point in the range of from about 135° C. to about 250° C.; wherein the polymer, the water, the polar organic solvent, and optionally the high-boiling solvent are present in such proportions that the polymer is dispersed in the multisolvent medium; and the composition forms a dust-free and tack-free film subsequent to being applied to the substrate, with the proviso that when the strong cationic groups are structural units formed from the polymerization of a vinylbenzyl trialkylammonium salt, a dialkylsulfonium salt, a benzylsulfonium salt, a cyclic sulfonium salt, a tri-$C_1$–$C_{18}$-alkyl-vinylbenzylphosphonium salt, a tri-$C_1$–$C_8$-aralkyl-vinylbenzylphosphonium salt, or a tri-$C_1$–$C_{18}$-arylvinylbenzylphosphonium salt, the multisolvent medium contains the high-boiling solvent.

The composition of the present invention can be designed to be irremovable, or easily removed without the use of harsh chemicals.

DETAILED DESCRIPTION OF THE INVENTION

The composition of the present invention comprises a polymer dispersed in a multisolvent medium that contains water and a low-boiling polar organic solvent which has at least one hydroxy group, is soluble in water in all proportions, and has a boiling point in the range of from about 70° C. to about 134° C.; wherein the polymer, the water, and the polar organic solvent are present in such proportions that the polymer is dispersed in the multisolvent medium, and the composition forms a dust-free and tack-free film subsequent to being applied to a substrate.

As used herein, the terms "dispersion" or "dispersed" refer to a stable or metastable mixture of the polymer with the multisolvent medium, and includes a solution, or a micellular or partially colloidal suspension. As used herein, a film or coating is "dust-free" when the finger, without pressure, can be lightly run over the surface of the film without picking up a film on the finger. As used herein, a film or coating is "tack-free" when the finger with a slight pressure will not leave a mark, and the surface is not sticky.

The polymer is characterized by containing structural units that can be formed from the polymerization of a polymerizable strong cationic monomer and a polymerizable acid monomer. As used herein, the term "polymerizable strong cationic monomer" refers to a monomer that contains ethylenic unsaturation and a cationic group having a charge that is independent of pH. Similarly, the term "polymerizable acid monomer" refers to a monomer that contains ethylenic unsaturation and an acid group. The term "structural units formed from the polymerization of . . . " is illustrated by the following example:

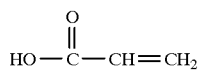

Acrylic Acid

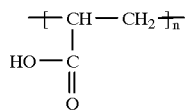

Structural units formed from the polymerization of Acrylic Acid

In addition to structural units formed from the polymerization of a polymerizable strong cationic monomer and a polymerizable weak acid monomer, the polymer also preferably includes structural units that can be formed from the polymerization of a polymerizable non-interfering monomer. The term "polymerizable non-interfering monomer" is used herein to refer to an uncharged monomer that does not adversely affect the formation and properties of a coating prepared from the dispersion of the polymer. As used herein, the term "dispersion" refers to a solution or a two-phase system, but not a stable aqueous dispersion or a latex.

Polymerizable acid monomers that are suitable for the preparation of the dispersion used to prepare the dust-free and tack-free coating include ethylenically unsaturated compounds having carboxylic acid, phenolic, thiophenolic, phosphinyl, sulfonic acid, sulfinic acid, phosphonic, or sulfonamide functionality. Preferred polymerizable acid monomers include acrylic acid, methacrylic acid, itaconic acid, β-carboxyethyl acrylate (usually as a mixture of acrylic acid oligomers), vinylbenzoic acid, vinylchlorophenol, vinylbromophenol, vinylthiophenol, 2-propenoic acid: 2-methyl-, (hydroxyphosphinyl) methyl ester, vinylphosphonic acid, 2-acrylamido-2-methyl-1-propane sulfonic acid, and 2-sulfoethyl-methacrylate. Acrylic acid, methacrylic acid, 2-acrylamido-2-methyl-1-propane sulfonic acid, and vinylphosphonic acid are more preferred acid monomers, and acrylic acid, methacrylic acid, and 2-acrylamido-2-methyl-1-propane sulfonic acid are most preferred.

The polymerizable strong cationic monomer is associated with a counterion, which may be, for example, halide such as chloride or bromide, nitrate, phosphate, or sulfate. Suitable polymerizable strong cationic monomers include salts of ethylenically unsaturated compounds having quaternary ammonium, sulfonium, cyclic sulfonium, and phosphonium functionality. Examples of suitable monomers having quaternary ammonium functionality include ethylenically unsaturated trialkylammonium salts such as vinylbenzyl tri-$C_1$–$C_4$-alkylammonium chloride or bromide; trialkylammoniumalkyl acrylates or methacrylates such as 2-[(methacryloyloxy)ethyl] trimethylammonium chloride and N,N-diethyl-N-methyl-2-[(1-oxo-2-propenyl)oxy] ethanaminium methyl sulfate (Chem. Abstracts Reg. No. 45076-54-8); and trialkylammoniumalkyl acrylamides such as N,N,N-trimethyl-3-[(2-methyl-1-oxo-2-propenyl) amino]-1-propanaminium chloride (Chem. Abstracts Reg. No. 51441-64-6) and N,N-dimethyl-N-[3-[(2-methyl-1-oxo-2-propenyl)amino]propyl]-benzenemethaminium chloride (Chem. Abstracts Reg. No. 122988-32-3). A preferred polymerizable quaternary ammonium salt is 2-[(methacryloyloxy)ethyl]trimethylammonium chloride.

Examples of polymerizable unsaturated sulfonium salts include dialkylsulfonium salts such as [4-ethoxy-3-(ethoxycarbonyl)-2-methylene-4-oxobutyl] dimethylsulfonium bromide (Chem. Abstracts Reg. No. 63810-34-4); and vinylbenzyl dialkylsulfonium salts such as vinylbenzyl dimethylsulfonium chloride. Examples of polymerizable cyclic sulfonium salts include 1-[4-[(ethenylphenyl)methoxy]phenyl]tetrahydro-2H-thiopyranium chloride (Chem. Abstracts Reg. No. 93926-67-1); and vinylbenzyl tetrahydrothiophenonium chloride, which can be prepared by the reaction of vinylbenzyl chloride with tetrahydrothiophene.

Examples of polymerizable phosphonium salts include 2-methacryloxyethyltri-$C_1$–$C_{20}$-alkyl-, aralkyl-, or arylphosphonium salts such as 2-methacryloxyethyltri-n-octadecylphosphonium halide (Chem. Abstracts Reg. No. 166740-88-1); tri-$C_1$–$C_8$-alkyl-, aralkyl-, or arylvinylbenzylphosphonium salts such as trioctyl-3-vinylbenzylphosphonium chloride, trioctyl-4-vinylbenzylphosphonium chloride (Chem. Abstracts Reg. No. 15138-12-4), tributyl-3-vinylbenzylphosphonium chloride, tributyl-4-vinylbenzylphosphonium chloride (Chem. Abstracts Reg. No. 149186-03-8), triphenyl-3-vinylbenzylphosphonium chloride, and triphenyl-4-vinylbenzylphosphonium chloride (Chem. Abstracts Reg. No. 145425-78-1); $C_3$–$C_{18}$-alkenyltrialkyl-, aralkyl-, or aryl-phosphonium salts such as 7-octenyltriphenylphosphonium bromide (Chem. Abstracts Reg. No. 82667-45-6); and tris(hydroxymethyl)-(1-hydroxy-2-propenyl)phosphonium salts (Chem. Abstracts Reg. No. 73082-48-1).

The polymer that contains pendant strong cationic groups and acid groups can also be prepared from a monomer that contains both an acid group and a strong cationic group. Examples of such monomers include N-(4-carboxy)benzyl-N,N-dimethyl-2-[(2-methyl-1-oxo-2-propenyl)-oxy] ethanaminium chloride and N-(3-sulphopropyl)-N-methacroyloxyethyl-N,N-dimethyl ammonium betaine.

It is also possible to prepare a polymer that contains strong cationic groups and acid groups by adding strong cationic functionality to an already prepared polymer. For example, a polymerizable monomer having a weak acid group can be copolymerized with a polymerizable non-interfering monomer containing an electrophilic group, such as vinylbenzyl halide or glycidyl methacrylate, to form a polymer having a weak acid group and an electrophilic group. This polymer can then be post-reacted with a nucleophile such as a tertiary amine, pyridine, a dialkyl sulfide, or a cyclic sulfide, which can displace the halide group or open the oxirane ring and form a benzylonium salt:

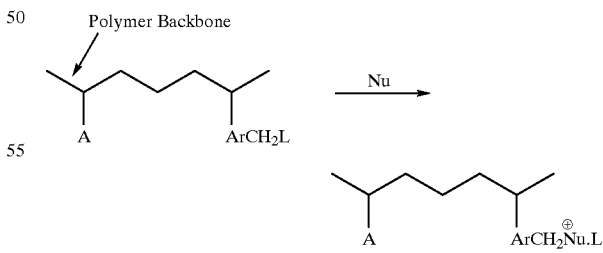

where A is a pendant weak acid group; Ar is an aromatic group, preferably a phenyl group; L is a leaving group, preferably a halide group, more preferably a chloride group; and Nu is the nucleophile.

In another example of adding strong cationic functionality to an already prepared polymer, a polymer backbone that contains pendant acid groups and a tertiary amine or a sulfide can be post-reacted with an alkylating reagent such as an alkyl halide to form a polymer that contains acid groups and strong cationic groups:

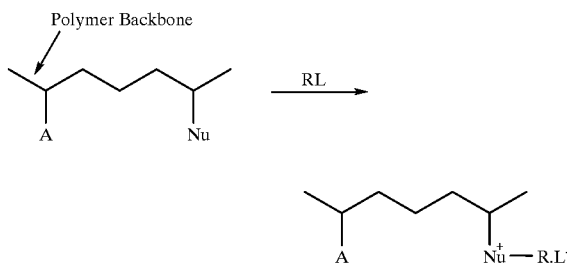

where RL is an alkylating reagent.

Examples of non-interfering polymerizable monomers include acrylates such as methyl acrylate, ethyl acrylate, butyl acrylate, 2-hydroxyethyl acrylate, 2-hydroxypropyl acrylate, glycidyl acrylate, and allyl acrylate; methacrylates such as methyl methacrylate, ethyl methacrylate, butyl methacrylate, allyl methacrylate, glycidyl methacrylate, 2-hydroxyethyl methacrylate, polypropylene glycol monomethacrylate, and 2-hydroxypropyl methacrylate; alkenyl aromatic hydrocarbons such as 4-methacryloxy-2-hydroxy-benzophenone, 2-(2'-hydroxy-5-methacrylyloxyethylphenyl)-2H-benzotriazole; and $C_1$–$C_4$ alkyl- or alkenyl-substituted styrenes, preferably styrene, α-methylstyrene, vinyltoluene, and vinylbenzyl chloride. Other examples of non-interfering species include $C_3$–$C_{18}$-perfluoroalkyl methacrylates such as 2-(perfluorooctyl)ethyl methacrylate; $C_3$–$C_{18}$-perfluoroalkyl acrylates such as 2-[ethyl[(heptadecafluorooctyl)sulfonyl]amino]ethyl 2-propenoate; and $C_3$–$C_{18}$-perfluoroalkyl vinylbenzenes. (See U.S. Pat. No. 4,929,666, column 4, lines 54 to 68, and column 5, lines 1 to 30.)

Preferably, the ratio of pendant acid groups to pendant strong cationic groups is not less than 0.5, more preferably not less than 0.75; and preferably not more than 5, more preferably not more than 2, and most preferably not more than 1.33.

The ratio of the structural units formed from the polymerization of the polymerizable non-interfering monomer to the sum of the structural units formed from the polymerization of the polymerizable acid monomer and the polymerizable strong cationic polymer varies depending on the percent solids of the composition, but is preferably not less than 70:30, more preferably not less than 80:20, and most preferably not less than 85:15; and preferably not greater than 99:1, and more preferably not greater than 98:2, and most preferably not greater than 95:5.

Typically the polymer has a number average molecular weight in the range of from about 1000 to about 200,000 Daltons, preferably from about 8000 to about 50,000 Daltons.

The composition includes water, a low-boiling polar organic solvent, optionally a high-boiling solvent having a boiling point in the range of from about 135° C. to about 250° C., and the polymer. Preferably, the composition contains not less than 10, more preferably not less than 20, and most preferably not less than 30 weight percent water; and preferably not greater than 98, more preferably not greater than 80, more preferably not greater than 70, and most preferably not greater than 60 weight percent water, based on the total weight of solvents and the polymer.

The low-boiling organic solvent preferably has a Hansen-based hydrogen bonding solubility parameter of from about 6.4 to about 10.5 cal/cm³, and the high-boiling solvent preferably has a Hansen-based hydrogen bonding solubility parameter of from about 1 to about 6.2 cal/cm³. Hansen-based solubility parameters are described in *Ind. Eng. Chem. Prod. Dev.*, Vol. 24, pg. 473 (1985), and in *J. Paint Technol.*, Vol. 39, pg. 505 (1967). Hydrogen bonding solubility parameter ($\delta_h$) relates to the nonpolar solubility parameter ($\delta_n$), and the polar solubility parameter ($\delta_p$) in the following manner:

$$\delta_h = (\delta_t^2 - \delta_n^2 - \delta_p^2)$$

and can be readily determined by one of ordinary skill in the art.

The low-boiling polar organic solvent is characterized by having at least one hydroxyl group, by being soluble in water in all proportions, and by having a boiling point in the range of from about 70° C. to about 134° C. Examples of preferred low-boiling organic solvents include ethanol, 1-propanol, 2-propanol, 2-methyl-2-propanol, 2-methyl-1-propanol, 1-butanol, and propylene glycol methyl ether. Preferably, the composition contains not less than 1, more preferably not less than 10, more preferably not less than 20, and most preferably not less than 30 weight percent of the low-boiling polar organic solvent; and preferably not greater than 80, more preferably not greater than 70, and most preferably not greater than 60 weight percent of the low-boiling polar organic solvent, based on the total weight of solvents and the polymer.

The high-boiling solvent, which is a preferred, but not an essential component of the composition, is characterized by having a boiling point in the range of from about 135° C. to about 250° C. Examples of preferred high-boiling solvents include benzonitrile, dimethyl succinate, dimethyl glutarate, dimethyl adipate, dipropylene glycol dimethyl ether, propylene glycol n-butyl ether, dipropylene glycol n-butyl ether, dipropylene glycol n-propyl ether, propylene glycol methyl ether acetate, dipropylene glycol dimethyl ether, dimethyl formamide, dimethylsulfoxide, propylene carbonate, N-methyl-2-pyrrolidone, ethylene glycol phenyl ether, diethylene glycol methyl ether, diethylene glycol n-butyl ether, ethylene glycol n-butyl ether, propylene glycol n-propyl ether, propylene glycol phenyl ether, dipropylene glycol methyl ether acetate, tripropylene glycol methyl ether, dipropylene glycol methyl ether and propylene carbonate.

The composition preferably contains not less than about 1, more preferably not less than 3, and most preferably not less than 5 weight percent of the high-boiling solvent; and preferably not greater than 75, more preferably not greater than 50, and most preferably not greater than 15 weight percent of the high-boiling solvent, based on the total weight of solvents and the polymer.

The amount of polymer contained in the composition depends on a variety of factors, including the nature of the monomers used to prepared the polymer, the solvents employed, as well as the end-use application. The amount of polymer is preferably not less than 0.5, more preferably not less than 2, more preferably not less than 5, and most preferably not less than 8 weight percent; and preferably not more than 50, more preferably not more than 25, and most preferably not more than 15 weight percent, based on the weight of the solvents and the polymer.

The polymer can be prepared by any suitable means, but is preferably prepared as a solution in the presence of a water-containing medium in which the polymer is soluble, such as water and 1-propanol. The polymer can be isolated in the counterion form or as the inner salt as illustrated by the following formulas:

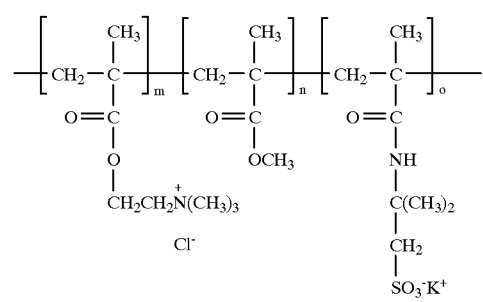

Counterion Form

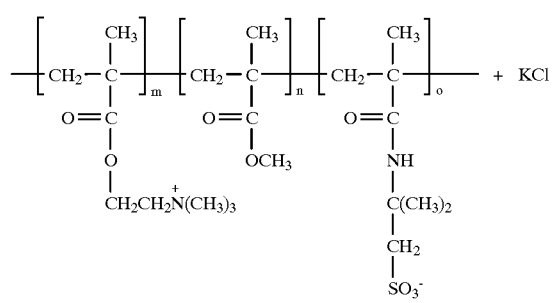

Inner Salt where m, n, and o are integers. When the polymer contains pendant weak acid groups, the inner salt can be isolated by precipitating the solution containing the polymer with an aqueous base such as aqueous sodium hydroxide or sodium carbonate. When the polymer contains pendant strong acid groups, water is sufficient to precipitate the inner salt.

The coatings described thus far are resistant to water, but can easily be removed with a mixture of solvents, preferably such as a combination of water and another solvent, more preferably water and I-propanol. These coatings can be rendered substantially permanent, that is, resistant to removal by organic solvents as well as aqueous-based acids or bases, in at least two ways. First, an effective amount of a crosslinking reagent, such as a melamine resin, an epoxy resin, or a diamine, may be added to react with the functional groups on the polymer to form a covalent crosslink; second, a polymerizable acid such as acrylic acid or methacrylic acid, may be added to the composition then subsequently cured; and third, the polymer may be designed to include a pendant crosslinkable functional group such as a polymerizable ethylenically or acetylenically unsaturated group, a sulfonium group, an epoxy group, or 2-oxazoline. An example of a preparation of a polymer that contains ethylenic unsaturation is illustrated as follows:

Polymer Backbone

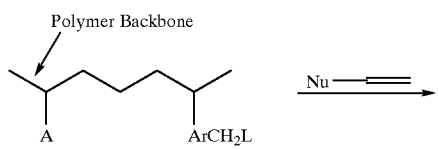

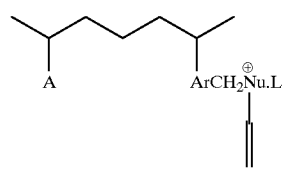

where Nu—= is a nucleophile (such as a tertiary amine or a sulfide) that contains ethylenic unsaturation; and A, Ar, and L are as previously defined. In the previous illustration, a polymerizable acid monomer, a polymerizable aryl halide, preferably vinylbenzyl chloride and a polymerizable non-interfering monomer are copolymerized to form a polymer having acid groups and benzyl halide groups. The polymer is then reacted with a nucleophile that contains ethylenic unsaturation to impart crosslinking capabilities to the polymer. An example of a suitable nucleophile with ethylenic unsaturation is the following compound:

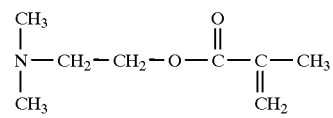

In the case where a polymerizable acid is used as the crosslinking agent, it is preferred that it be added to the inner salt to form a crosslinkable polymer as shown in the following illustration:

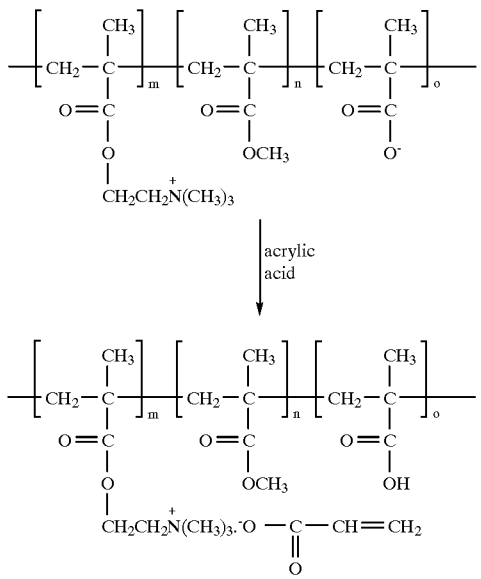

Another example of a polymer that includes a pendant crosslinkable group is a polymer formed by the copolymerization of 2-isopropenyl-2-oxazoline with the polymerizable strong cation monomer and the polymerizable acid monomer.

When the composition that contains includes a crosslinking agent or a crosslinkable functional group is coated onto a substrate, the coating is advantageously allowed to become dust-free and tack-free before means such as heating or UV radiation is used to promote crosslinking.

The compositions of the present invention can be used, for example, to coat or protect floors, automobile parts, human skin, countertops, wood, furniture, and the interiors or exteriors of houses. The compositions may also include additives such as pigments, dyes, fungicides, or bacteriacides.

The following examples are for illustrative purposes only and are not intended to limit the scope of this invention. All percentages are by weight unless otherwise noted.

EXAMPLE 1

Preparation of a 10 Weight Percent Polymer in Water/1-Propanol/Propylene Carbonate Medium and a Coating Therefrom Four liquid streams were simultaneously and continuously added to a reaction vessel maintained with stirring at 60° C. under nitrogen, and containing water (30 g) and 1-propanol (30 g). The streams were added over a 5-hour period using 100-mL syringes driven by a Sage Instruments syringe pump Model 355 (Cole-Palmer Instrument Company). After the addition was completed, the reaction was maintained at 60° C. for an additional hour. The contents of the four streams are shown in Table 1.

TABLE 1

| Stream No. | Component | Amount | |
|---|---|---|---|
| 1 | Methyl Methacrylate | 100.45 | g (1.00 mol) |
|   | Acrylic Acid | 5.9 | g (0.082 mol) |
| 2 | M-Quat[a] | 18.2 | g (13.5 g active, 0.065 mol) |
|   | Water | 75 | g |
| 3 | Polypropylene Glycol Monomethacrylate | 19.8 | g (0.022 mol) |
| 4 | VAZO ™ 52[b] | 1.00 | g |
|   | 1-Propanol | 75 | g |

[a]2-[(methacryloyloxy)ethyl]trimethylammonium chloride obtained as a 74 percent aqueous solution from Bimax Inc., 717 Chesapeake Ave., Baltimore, MD 21225
[b]2,2'-azobis(2,4-dimethylpentane nitrile) obtained from E. I. duPont de Nemours & Co., Inc.

The polymer solution was cooled and removed from the reactor, and precipitated in a 0.1 M aqueous solution of sodium carbonate. A solid polymer was collected and washed several times with water, then dried at 70° C. for 24 hours. The dried polymer was dissolved in a multisolvent medium consisting of 10 weight percent polymer, 10 weight percent propylene carbonate, 40 weight percent 1-propanol, and 40 weight percent water. Performance of the composition was evaluated on a black auto panel (batch number 50225511, supplied by ACT Laboratories Inc., Hillsdale, Mich.) by drawing down a thin coating of the composition with a KIMWIPES® EX-L wiper (a trademark of Kimberly-Clark Corp.). The film was allowed to dry for 24 hours, then tested by a wipe test using water and a cotton swab. The film was wiped more than 80 times before coming off the substrate.

EXAMPLE 2

The procedure for preparing the polymer that was used in Example 1 was repeated except that the distribution of monomers was altered according to Table 2.

TABLE 2

| Stream No. | Component | Amount | |
|---|---|---|---|
| 1 | Methyl Methacrylate | 78.1 | g (0.780 mol) |
|   | Acrylic Acid | 7.95 | g (.110 mol) |
| 2 | M-Quat | 30.9 | g (22.9 g active, 0.110 mol) |
|   | Water | 75 | g |
| 3 | Polypropylene Glycol Monomethacrylate | 19.8 | g (0.022 mol) |
| 4 | VAZO ™ 52 | 1.00 | g |
|   | 1-Propanol | 75 | g |

After completion of the reaction, a portion of the reaction mixture (40 g, directly out of the reactor) was combined with propylene carbonate (10 g), water (25 g) and 1-propanol (25 g) to form a solution. A portion of this solution was applied to the black auto panel with a tissue as before. After 15 minutes, the clear coating withstood 20 wipes (with a vertical force of about 1000 g) using a water-wet cotton-tipped applicator.

EXAMPLE 3

Preparation of a 10 Weight Percent Polymer in Water/1-Propanol/Propylene Glycol n-Butyl Ether Medium and a Coating Therefrom A 10 weight percent solution of a polymer prepared from a molar equivalent ratio of 76.0 percent methyl methacrylate, 10 percent 2-hydroxy ethyl methacrylate, 7.0 percent M-Quat, and 7.0 percent 2-acryliamido-2-methylpropane sulfonic acid was prepared by adding 10 g of the dried polymer (i.e., polymer having the polymerization solvent removed therefrom) to 90 g of a 10:50:40 weight percentage mixture of propylene glycol n-butyl ether:1-propanol:water. A portion of the resulting formulation was applied to an auto panel using a single KIMWIPE® EXL wiper. After 3 minutes, the coating was tack-free and resistant to running water, but could be removed by wiping with a cotton swab wetted with a 1:1 weight ratio of water and ethanol.

About 0.1 g of a melamine-formaldehyde crosslinking agent (RESIMENE® 717, obtained from Monsanto Co., St. Louis, Mo.) was added to 9 g of the above polymer-solvent formulation. The crosslinker-containing formulation was applied to the auto panel as before, and the coating was cured at 130° C. for 30 minutes. The resultant coating was resistant to greater than 100 wipes with 1:1 ethanol:water or methylethyl ketone.

EXAMPLE 4

Preparation of a 10 Weight Percent Polymer in Water 1-Propanol and a Coating Therefrom Five streams are continuously and simultaneously added to the reaction vessel conditions as described in Example 1. The contents of the five streams are shown in Table 4.

TABLE 4

| Stream No. | Component | Amount | |
|---|---|---|---|
| 1 | Methyl Methacrylate | 81.1 | g (0.81 mol) |
| 2 | ZONYL ® TM Fluoromethacrylate NMP | 5.1 | g |
|   |   | 25 | g |

TABLE 4-continued

| Stream No. | Component | Amount |
|---|---|---|
| 3 | M-Quat | 19.4 g (14.5 g active, 0.07 mol) |
| | Water | 75 g |
| 4 | 2-Acryliamido-2-Methylpropane Sulfonic Acid | 14.5 g (0.07 mol) |
| 5 | VAZO ™ 52 | 1.00 g |
| | 1-Propanol | 75 g |

Polymer was precipitated from the solution by adding the solution with agitation to four liters of water. After 12 hours, the precipitate was filtered and added to three liters of water. After an additional 12 hours, the precipitate was filtered and washed repeatedly with water. The water-washed precipitate was then dried in an oven at 50° C. for 12 hours. The dried polymer was ground with a mortar and pestle, and a portion (0.2 g) was dissolved in a solution containing 1.4 g 1-propanol and 0.6 g water. A portion of the solution was applied to the auto panel as before, and after 3 minutes (relative humidity of 46 percent and at 23° C.), a dust-free and tack-free coating formed. The coating was washed with cool running water (15° C.) for 1 minute, and then wiped dry. The resulting coating withstood 40 wipes (with a vertical force of about 1000 g) using a water-wet cotton-tipped applicator. When the coating was washed with hot running water (70° C.) for 1 minute before being wiped, the resulting coating withstood 100 wipes.

What is claimed is:

1. A composition comprising:
   a) a polymer that contains strong cationic groups and acid groups; and
   b) a multisolvent medium that contains water, a low-boiling polar organic solvent which has at least one hydroxy group, is soluble in water in all proportions, and has a boiling poing in the range of from about 70° C. to about 134° C.; and a high-boiling solvent, which has a boiling point in the range of from about 135° C. to about 250° C.;
wherein the polymer, the water, the polar organic solvent, and the high-boiling solvent are present in such proportions that the polymer is dispersed in the multisolvent medium.

2. The composition of claim 1 wherein the polymer further contains structural units formed from the polymerization of a polymerizable non-interfering monomer.

3. The composition of claim 2 wherein the non-interfering polymerizable monomer is selected from the group consisting of methyl acrylate, ethyl acrylate, butyl acrylate, 2-hydroxyethyl acrylate, 2-hydroxypropyl acrylate, allyl acrylate, glycidyl acrylate, methyl methacrylate, ethyl methylacrylate, butyl methacrylate, allyl methacrylate, glycidyl methacrylate, 2-hydroxyethyl methacrylate, 2-hydroxypropyl methacrylate, polypropylene glycol monomethacrylate, a $C_3-C_{18}$-perfluoroalkyl methacrylate, a $C_3-C_{18}$-perfluoroalkyl acrylate, a $C_3-C_{18}$-perfluoroalkyl vinylbenzene, styrene, α-methylstyrene, and vinyltoluene.

4. The composition of claim 2 wherein the acid groups are structural units formed by the polymerization of a monomer selected from the group consisting of acrylic acid, methacrylic acid, itaconic acid, β-carboxyethyl acrylate, vinylbenzoic acid, vinylphosphonic acid, 2-acrylamido-2-methyl-1-propanesulfonic acid, 2-sulfoethylmethacrylate, and 2-propenoic acid: 2-methyl-, (hydroxyphosphinyl) methyl ester.

5. The composition of claim 2 wherein the strong cationic groups are structural units formed by the polymerization of a monomer selected from the group consisting of a trialkylammoniumalkyl acrylate; a trialkylammoniaymalkyl methacrylate, a trialkylammoniumalkyl acrylamide, a dialkylsulfonium salt, a benzylsufonium salt, a cyclic sulfonium salt, a 2-methacryloxy-ethyltri-$C_1-C_{20}$-alkylphosphonium salt, a 2-methacryloxyethltri-$C_1-C_{20}$-aralkyl-phosphoniumsalt, a 2-methacryloxyethytri-$C_1-C_{20}$-arylphosphonium salt, a tri-$C_1-C_{20}$-alkyl-vinlybenzylphosphnium salt, a tri-$C_1-C_{18}$-aralkyl-vinylbenzylphosphonium salt, a tri-$C_1-C_{18}$-aryl-vinylbenzylphosphonium salt, a $C_3-C_{18}$-alkenyltrialkyl-phosphonium salt, a $C_3-C_{18}$-aralkyl-phosphonium, salt and a $C_3-C_{18}$-aryl-phosphonium salt.

6. The composition of claim 3 wherein the non-interfering polymerizable monomer is methyl methacrylate, butyl acrylate, 2-hydroxyethyl methacrylate, 4-methacryloxy-2-hydroxy-benzophenone, polypropylene glycol monomethacrylate, or 2-(2'-hydroxy-5-methacrylyloxyethylphenyl)-2H-benzotriazole.

7. The composition of claim 2 wherein the ratio of structural units formed from the polymerzation of the polymerizable non-interfering monomer to the strong catonic groups and the acid groups is from about 70:30 to about 98:2.

8. The composition of claim 5 wherein the ratio of structural units formed from the polymerization of the polymerizable non-interfering monomer to the strong catonic groups and the acid groups is from about 85:15 to about 95:5.

9. The composition of claim 8 wherein the strong catonic group is formed by the polymerization of an ethylenically unsaturated quaternary ammonium salt associated with a chloride, bromide, nitrate, phosphate, or sulfate counterion.

10. The composition of claim 9 wherein the quaternary ammonium salt is 2-((methacryloyloxy)ethyl) trimethylammonium chloride; the acid groups are structural units formed from the polymerization of a monomer selected from the group consisting of acrylic acid, methacrylic acid, and 2-acrylamido-2-methyl-1-propanesulfonic acid; and the non-interfering polymerizable monomer is selected from the group consisting of polypropylene glycol monomethacrylate, methyl methacrylate, and butyl acrylate.

11. The composition of claim 2 wherein the low-boiling polar organic solvent has a hydrogen solubility parameter of from 6.4 to 10.5, and the high-boiling solvent has a hydrogen bonding solubility parameter of from about 1 to 6.2.

12. The composition of claim 11 wherein the low-boiling polar organic solvent is selected from the group consisting of 1-propanol, 2-methyl-2-propanol, 2-propanol, 1-butanol, and propylene glycol methyl ether.

13. The composition of claim 11 wherein the high-boiling solvent is selected from the group consisting of benzonitrile, dimethyl succinate, dimethyl glutarate, dimethyl adipate, dipropylene glycol dimethyl ether, propylene glycol n-butyl ether, dipropylene glycol n-butyl ether, dipropylene glycol n-propyl ether, propylene glycol methyl ether acetate, dipropylene glycol dimethyl ether, dimethyl formamide, dimethylsulfoxide, N-methyl-2-pyrrolidone, ethylene glycol pheny ether, diethylene gylcol methyl ether, diethylene glycol n-butyl ether, ethylene glycol n-butyl ether, propylene glycol n-propyl ether, propylene glycol phenyl ether, dipropylene glycol methyl ether acetate, tripropylene glycol methyl ether, dipropylene glycol methyl ether and propylene carbonate.

14. The composition of claim 12 wherein the high-boiling solvent is dipropylene glycol dimethyl ether, propylene glycol n-butyl ether, or propylene carbonate.

15. The composition of claim 14 wherein the amount of water in the multisolvent medium is in the range of from about 10 to about 80 percent, the amount of the low-boiling polar organic solvent is in the range of from about 10 to about 80 percent, the amount of the high-boiling solvent is in the range of from about 1 to about 50 percent, and the amount of the polymer is in the range of from about 0.5 to about 50 percent, based on the weight of the water, the low-boiling polar organic solvent, the high-boiling point solvent, and the polymer.

16. The composition of claim 10 wherein the amount of water in the multisolvent medium is in the range of from about 30 to about 60 percent, the amount of the low-boiling polar organic solvent is in the range of from about 30 to about 60 percent, the amount of the high-boiling solvent is in the range of from about 3 to about 15 percent, and the amount of the polymer is in the range of from about 0.2 to about 15 percent, based on the weight of the water, the low-boiling polar organic solvent, and the high-boiling point solvent.

17. The composition of claim 16 wherein the low-boiling polar organic solvent is 1-propanol and the high-boiling solvent is propylene carbonate or propylene glycol n-butyl ether.

18. The composition of claim 2 which further includes an effective amount of a crosslinking agent to cause the subsequently-formed film to become substantially permanent upon application of heat or UV light.

19. The composition of claim 18 wherein the crosslinking agent is a melamine resin, an epoxy resin, a diamine, methacrylic acid, or acrylic acid.

20. The composition of claim 2 wherein the polymer further includes crosslinkable ethylenically unsaturated structural units.

* * * * *